United States Patent
Slocum et al.

(10) Patent No.: US 8,308,681 B2
(45) Date of Patent: Nov. 13, 2012

(54) DEVICE FOR MIXING AND DELIVERING FLUIDS FOR TISSUE REPAIR

(75) Inventors: Alexander Slocum, Bow, NH (US); Matthew R. Carvey, Bedford, MA (US); Alexey Salamini, Hermosa Beach, CA (US); Daniel G. Walker, Cambridge, MA (US); Ying-Chih Wang, Cambridge, MA (US); Martha M. Murray, Sherborn, MA (US)

(73) Assignee: Children's Medical Center Corporation, Boston, MA (US)

(*) Notice: Subject to any disclaimer, the term of this patent is extended or adjusted under 35 U.S.C. 154(b) by 944 days.

(21) Appl. No.: 11/883,985

(22) PCT Filed: Feb. 9, 2006

(86) PCT No.: PCT/US2006/004445
§ 371 (c)(1),
(2), (4) Date: Jul. 3, 2008

(87) PCT Pub. No.: WO2006/086479
PCT Pub. Date: Aug. 17, 2006

(65) Prior Publication Data
US 2009/0143765 A1   Jun. 4, 2009

Related U.S. Application Data

(60) Provisional application No. 60/651,329, filed on Feb. 9, 2005.

(51) Int. Cl.
*A61M 37/00* (2006.01)
(52) U.S. Cl. .................................................. 604/82
(58) Field of Classification Search .............. 604/264, 604/523–529, 82, 542, 152; 600/153, 581; 623/23.51, 23.72; 239/304
See application file for complete search history.

(56) References Cited

U.S. PATENT DOCUMENTS

| | | | |
|---|---|---|---|
| 3,373,906 A | 3/1968 | De Hart et al. | |
| 3,587,982 A | 6/1971 | Campbell | |
| 3,738,535 A | 6/1973 | Nicholls | |
| 3,774,604 A * | 11/1973 | Danielsson | 604/167.05 |
| 4,069,814 A * | 1/1978 | Clemens | 600/581 |
| 4,265,618 A * | 5/1981 | Herskovitz et al. | 433/32 |
| 4,753,536 A | 6/1988 | Spehar et al. | |

(Continued)

FOREIGN PATENT DOCUMENTS
EP    0 445 951 A2    9/1991
(Continued)

*Primary Examiner* — Manuel Mendez
(74) *Attorney, Agent, or Firm* — Wolf, Greenfield & Sacks, P.C.

(57) ABSTRACT

A device for mixing and delivering a mixture of fluids to a target site includes a tube for containing the mixture. A compressible auger for mixing the fluids is movably disposed within the tube, one end of the auger being free at the distal end of the tube. A plunger is also movable within the tube in communication with the other end of the auger. When the plunger is moved axially within the tube the auger also moves axially and the auger is compressed to dispense the fluid. The mixing and delivery device can be used with an apparatus for the arthroscopic delivery of a tissue repair material to a repair site. The apparatus includes a first sheath and a second sheath removably attached to the first sheath for delivering the tissue repair material to the repair site.

23 Claims, 12 Drawing Sheets

U.S. PATENT DOCUMENTS

| | | | |
|---|---|---|---|
| 4,808,184 A | 2/1989 | Tepic | |
| 4,932,942 A | 6/1990 | Maslanka | |
| 5,037,396 A * | 8/1991 | Streeter | 604/152 |
| 5,119,669 A | 6/1992 | Silvis et al. | |
| 5,152,462 A * | 10/1992 | Evans | 239/304 |
| 5,380,087 A | 1/1995 | Haber et al. | |
| 5,503,616 A * | 4/1996 | Jones | 600/153 |
| 6,139,520 A * | 10/2000 | McCrory et al. | 604/60 |
| 6,234,795 B1 | 5/2001 | Fischer | |
| 6,309,372 B1 | 10/2001 | Fischer et al. | |
| 6,454,129 B1 | 9/2002 | Green | |
| 6,699,214 B2 * | 3/2004 | Gellman | 604/82 |
| 6,964,685 B2 | 11/2005 | Murray et al. | |
| 6,971,787 B2 | 12/2005 | Botrie et al. | |
| 7,156,880 B2 * | 1/2007 | Evans et al. | 623/23.51 |
| 7,901,461 B2 * | 3/2011 | Harmon et al. | 623/23.72 |
| 2003/0167053 A1 * | 9/2003 | Taufig | 604/542 |
| 2004/0059416 A1 | 3/2004 | Murray et al. | |
| 2004/0262332 A1 | 12/2004 | Pauser et al. | |
| 2005/0230422 A1 | 10/2005 | Muller et al. | |
| 2005/0261736 A1 | 11/2005 | Murray et al. | |

FOREIGN PATENT DOCUMENTS

| | | |
|---|---|---|
| GB | 2 106 794 | 4/1983 |
| WO | 00/74760 A2 | 12/2000 |
| WO | 2004078134 A2 | 9/2004 |

* cited by examiner

DEVICE FOR MIXING AND DELIVERING FLUIDS FOR TISSUE REPAIR

RELATED APPLICATIONS

This application is a National Stage Application of PCT/US2006/004445 which claims priority under 35 U.S.C. §119(e) to U.S. Provisional Application Ser. No. 60/651,329, entitled "DELIVERY DEVICE FOR TISSUE REPAIR" filed on Feb. 9, 2005.

BACKGROUND OF THE INVENTION

1. Field of the Invention

The present invention relates to a device for mixing and delivering viscous fluids for tissue repair, and more particularly, to a device for arthroscopically delivering a scaffold of platelet rich plasma and collagen mixture to repair the tissue.

2. Description of the Related Art

Over half a million people in the U.S. suffer an intra-articular injury every year. Approximately 100,000 of the injuries are due to a tear in the anterior cruciate ligament (ACL) in the knee. Over 500,000 injuries are caused by meniscal tears.

Various procedures have been developed to repair a damaged ligament. For example, one method of repairing a torn or ruptured ACL requires a tunnel to be drilled in both the tibia and the femur. A substitute ACL graft is inserted to extend from one tunnel to another and the ends of the graft are secured to the walls of the tunnel using interference screws or the like. The necessary incisions are large and invasive. Procedure and recovery times for such a procedure are extensive.

Biologically, the ACL and other intra-articular tissues do not heal easily. Typically, the ACL has an impaired response to the injury. Blood clots, which are the foundation for the healing, cannot form in the knee joint. Moreover, physical reconstruction is difficult. One reason is the elasticity. An ACL has a Young's modulus of approximately 1 GPa. For reference, steel has a typical modulus of approximately 200 GPas.

Another problem with traditional joint tissue repair procedures, including treatment of the ACL, meniscus and articular cartilage are the amount of instruments, and incisions therefor, that are required. In addition to the surgical instruments, the physician may also need to use an arthroscope to view the surgical field. The instrumentation is costly.

Thus, there is a need to provide a more simple, less invasive and enhanced procedure to repair injured tissue.

SUMMARY OF THE INVENTION

One aspect of the present invention is to enhance tissue repair by using a bioactive scaffold, which stimulates healing of the tissues.

Another aspect of the present invention is to deliver the scaffold arthroscopically using a minimally invasive technique that will decrease operative complications and speed patient recovery.

Yet another aspect of the present invention is to provide a scaffold that has been thoroughly mixed and delivered at a precise viscosity and temperature.

Still another aspect of the invention is to mix and dispense the scaffold with a device that is easy to maneuver, control and use in a sterile environment.

In accomplishing these and other aspects of the present invention there is provided a device for mixing and delivering a mixture of fluids to a target site. The device includes a tube for containing the mixture. The tube has a proximal and a distal end. A compressible auger for mixing the fluids is movably disposed within the tube, one end of the auger being free at the distal end of the tube. A plunger is also movable within the tube. A first end of the plunger is in communication with the other end of the auger and a second end of the plunger extends from the proximal end of the tube. When the plunger is moved axially within the tube the auger also moves axially and the auger is compressed.

In accomplishing these and other aspects of the present invention there is also provided a device to be disposed on an arthroscopic sheath for mixing and delivering viscous fluids for the arthroscopic repair of tissue. The device includes a secondary elongated sheath removably disposed along an axial length of the arthroscopic sheath and has opposed ends. One of the ends of the secondary sheath has a tip located at an operating end of the arthroscopic sheath.

In accomplishing these and other aspects of the present invention there is provided a device for mixing and delivering viscous fluids for the repair of tissue. The device includes a barrel having opposed ends. A mixing and delivery device is disposed on the barrel in communication with the injector. The mixing and delivery device includes a tube for containing the fluids. An auger is movably disposed within a mixing chamber of the tube for mixing the fluids. A plunger is movably disposed within the tube for delivering a mixture of the fluids to an injector. A handle is disposed at the other end of the barrel. A trigger mechanism is movably mounted on the barrel for actuating the plunger to move the same within the tube to deliver the mixture to the injector. A dryer mechanism is located in the barrel in communication with the injector for removing excess fluid from the injury site. A heater located on the barrel heats one or more of the fluids.

There is also provided a method for repairing an injured tissue including the steps of providing a tube having a plunger movably disposed therein for receiving a plurality of fluids to be mixed. The tube has a mixing chamber for containing the fluids, and a collapsible auger movably disposed within the mixing chamber of the tube for mixing the fluids. An injector is attached at one end of the tube, the injector being in fluid communication with the mixing chamber. The mixing chamber of the tube is loaded with a desired amount of each of the fluids. The auger is rotated to mix the fluids. The mixture of fluids is heated and the injury site is dried to remove any excess moisture. The injector is inserted into the patient and the mixture is injected through the injector to the injury site.

These and other features, aspects, and advantages of the present invention will become more apparent from the following detailed description of the preferred embodiment relative to the accompanied drawings, in which:

DETAILED DESCRIPTION OF THE PREFERRED EMBODIMENTS

Figure 1:
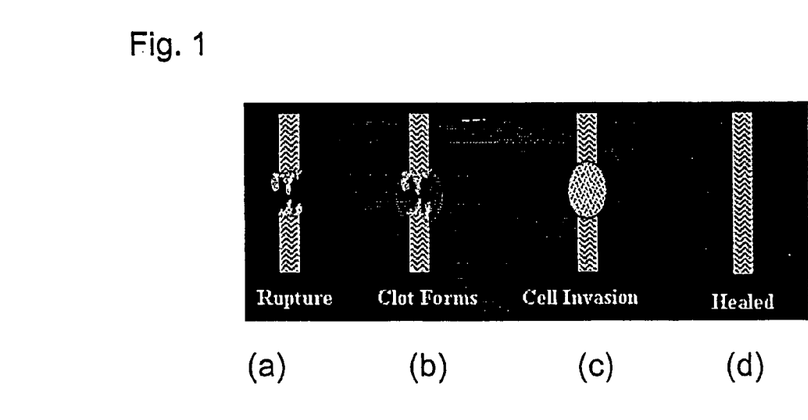
FIG. 1 illustrates the healing process of an injured tissue according to the present invention.

The present invention relates to enhancing tissue repair by using a bioactive scaffold that stimulates healing of the tissue, for example, an ACL. The scaffold consists of a viscous fluid mixture of platelets rich plasma (PRP) and soluble collagen gel. Together the mixture forms a glue, which when delivered arthroscopically to the injury fills the wound site and serves as a provisional scaffold on which healing can proceed. As shown in FIG. 1 (a)-(d), the mixture of fluids is delivered to a rupture in the ligament. The mixture includes platelets and collagen. Collagen can be made from tissue rich in collagen including ligament, tendon, skin, fascia, or scar tissue. The mixture acts as a bridge to glue the tear. Cells invade the mixture and eventually the tear heals. Although the fluid mixture is described as platelet rich plasma and collagen, it should be appreciated that other fluids, gels and mixtures are contemplated by the present invention.

The present invention provides an enhanced arthroscopic device and system for repairing a ligament or other injured tissue in a sterile environment. Two or more viscous fluids are blended to a microscopic level. Viscosity control requires that the injected fluid not be too runny as to drip off of the ligament, but not to viscous as to be damaged on injection.

Figure 2:
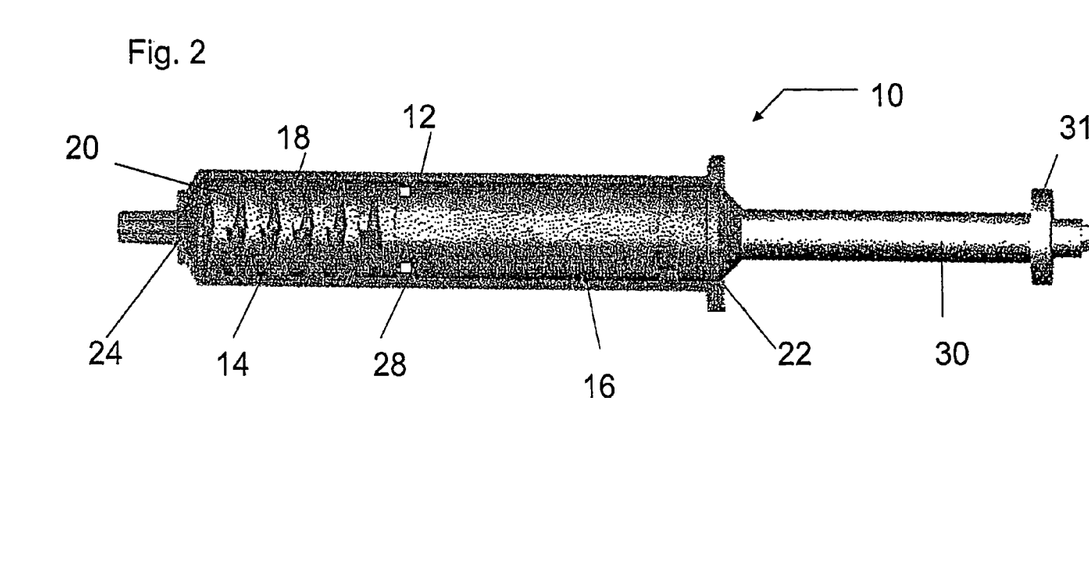
FIG. 2 is a cross-sectional view of the mixing and delivery device of the present invention.

Referring to FIG. 2, a delivering and mixing device 10 includes a hollow tube or syringe 12, a mixing element 14 and a plunger 16. As will be described further herein, mixing element 14 and plunger 16 are axially and rotatably movable within tube 12. A mixture of fluids 20 is contained in a mixing chamber 18 formed by the sealed engagement of plunger 16 and an inner diameter of tube 12.

Figure 3:
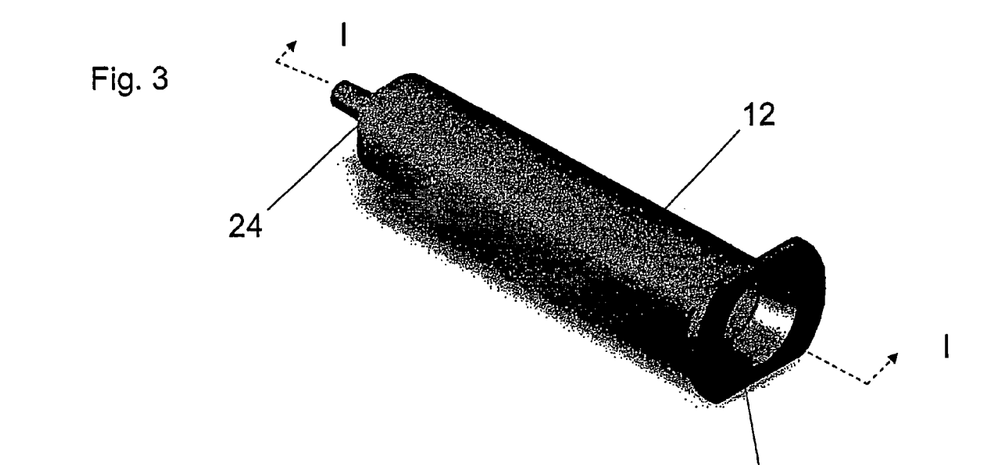
FIG. 3 is a perspective view of the mixing tube of the present invention.
Figure 4:
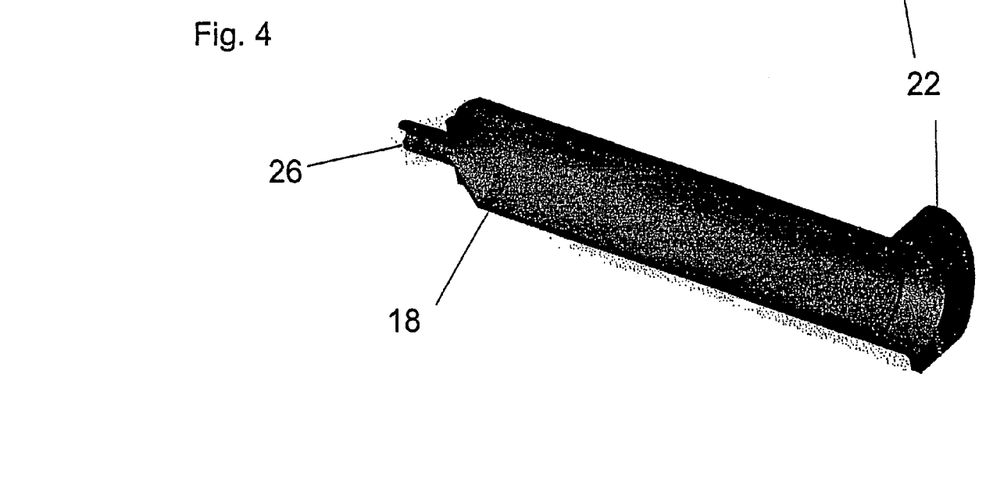
FIG. 4 is a cross-sectional view of the tube of FIG. 3 taken along line I-I.

As shown in FIGS. 3 and 4, tube 12 has a proximal end 22 and a distal end 24. Proximal end 22 is sized to receive mixing element 14 and plunger 16. Located at distal end 24 is a discharge opening 26 that communicates with mixing chamber 18. As will be described further herein, when auger 14 and plunger 16 are moved axially within tube 12 toward end 24 the mixture contained within chamber 18 is dispensed through discharge opening 26.

In one embodiment mixing element 14 is a collapsible or compressible auger. Auger size, clearance and pitch are chosen to optimize auger geometry. Tooth profile, lead angle, thickness, width, clearance and length are some key mixing parameters. For example, a lead angle of 5-10 rotations per inch with a tall, narrow tooth profile is acceptable. Further optimization of such parameters can reduce the mixing time below 20-30 seconds.

The collapsible auger is derived from a rectangular cross-section spring. As will be described further herein, it is attached at the front of the plunger, and free to move axially at the other end. The torsional stiffness of the spring allows it to resist loading from the mixing of the fluids without significant deformation. Unlike a conventional auger, however, it can be compressed by a plunger from behind. This eliminates a significant portion of the dead volume between the threads of the auger, and so maximizes the amount of injected fluid. As shown in FIG. 2, the plunger seals both the outer casing, and the auger shaft to prevent leakage of the fluid. The auger shaft is constrained axially, so movement of the plunger pushing on the free end of the auger acts to compress it.

A number of additional active-type mixing elements are available. Active mixing uses a moving element inside the fluid reservoir to force the fluids to interact. In this strategy, the mixing quality is determined by the length of time and type of moving element. These include helical impellers, anchors, open impellers, whips and the mechanical equivalents thereof. Helical impellers are of a spiral-type design with a relatively large surface area, and include augers. Anchors resemble a fisherman anchor, with two arms forming a u-shape. Impellers have a similar shape as propellers, but are used for internal flow. Whips can be mixing elements having an eccentric mixing portion. Once again it should be appreciated that the present invent contemplates passive and vibrational mixing, as well as the above-described active mixing.

Passive mixing uses a dividing helix, or similar device, to mix the fluid as it flows through a tube. In this strategy, the mixing quality is determined by the length and fineness of the mixing section. Vibrational mixing can include the introduction of metal spheres into a mixing tube, with a vibrator on the outside. The vibrator forces the spheres to shake and mix the fluids. Another type of vibration mixing is vortex shaking and is considered the medical industry standard for mixing low viscosity fluids.

Figures 5, 6, 7:
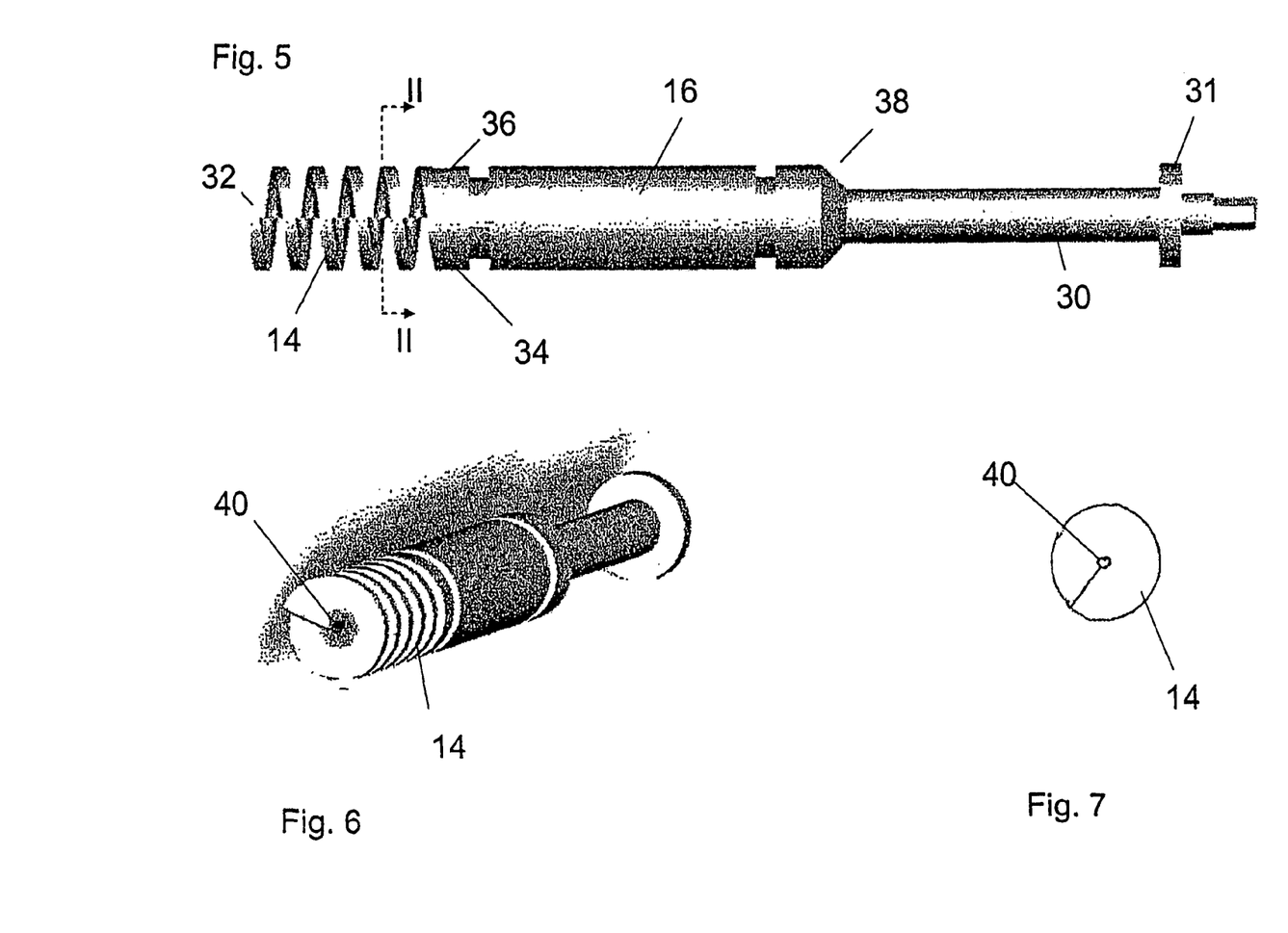
FIG. 5 is a side view of the mixing element of the present invention.
FIG. 6 is a perspective view of the mixing element of FIG. 5.
FIG. 7 is a cross-sectional view of the mixing element taken along line II-II of FIG. 6.

Referring to FIG. 5, mixing element or auger 14 has a first end 32 and a second end 34. When auger 14 is located within tube 12, end 32 is freely disposed at distal end 24 of the tube. End 34 of the auger can be fixed to a first end 36 of plunger so that auger 14 is integrally formed with plunger 16. It should be appreciated that elements 14 and 16 can be formed separately as well and attached together via other conventional manners. The other end 38 of plunger 16 extends from proximal end 22 of tube 12.

Referring back to FIG. 2, there is limited clearance between the outer diameter of auger 14 and the tube inner diameter. A fluid return path exists therebetween and ensures that the fluids did not remain stratified. As shown in FIGS. 6 and 7, auger 14 also includes an internal discharge passage 40 that extends along its axial length. Discharge passage 40 also acts as a fluid passage for the mixture. The outer diameter of discharge passage 40 may be less than an inner diameter of tube discharge opening 26.

When plunger 16 is activated and moved axially toward the discharge opening of the tube free end 32 of the auger abuts against distal end 24 of the tube and the auger is compressed or collapsed to discharge the mixture from tube 12. To prevent leakage of the mixture during dispensing at least one seal 28, such as an o-ring, can be located between the plunger and an inner diameter of the tube.

In addition to pushing the mixture from tube 12, displacing the mixture by blowing a secondary fluid can also be done. Moreover, squeezing the mixture by using a reduction in a flexible container volume by a applying a force on the outside is contemplated. Pumping is another mixture delivery method, as is spinning the auger backwards. This would force the fluid towards the front of the auger and out of the tube.

In addition to being axially movable within tube 12, auger 14 and plunger 16 are also rotatable within the tube. As shown in FIG. 5, plunger 16 includes a shaft 30 that extends from end 38. Shaft 30 is connected to a motor to rotate the same. The auger and plunger can be driven by a small motor, for example, a Mabuchi RE-260 hobby motor with a 5.25:1 gear reduction.

An injector 42 (FIG. 9), such as a needle, is located in the discharge opening 26 of the tube. The mixing chamber of tube 12 can be preloaded with a quantity of a first fluid component, for example, collagen. The tube or syringe can be capped and the assembly placed in a sterile pack or kit. Later, for example at an operation site, platelets can be extracted from the patient immediately prior to the procedure and the platelets and plasma delivered to the mixing chamber by uncapping the tube and inserting the injector into the fluid and drawing the fluid through the injector by movement of the plunger. In another embodiment, the mixing chamber of the syringe could have two compartments separated by a membrane. One of the compartments could be loaded with unneutralized collagen and one with a neutralization solution. When the membrane is broken, for example by the spinning motion of the mixing element. Alternatively, the membrane could be made of a dissolvable material, such as a material that dissolves at room temperature. Upon disruption of the membrane, the two fluids could be mixed, for example, just before drawing in the PRP. Additionally, the plunger could be activated to move only half-way to draw up one component, and then drawn completely up to add the second component. Alternatively, the fluid could be tapped down and air purged before drawing in the other fluid.

Figure 8A:
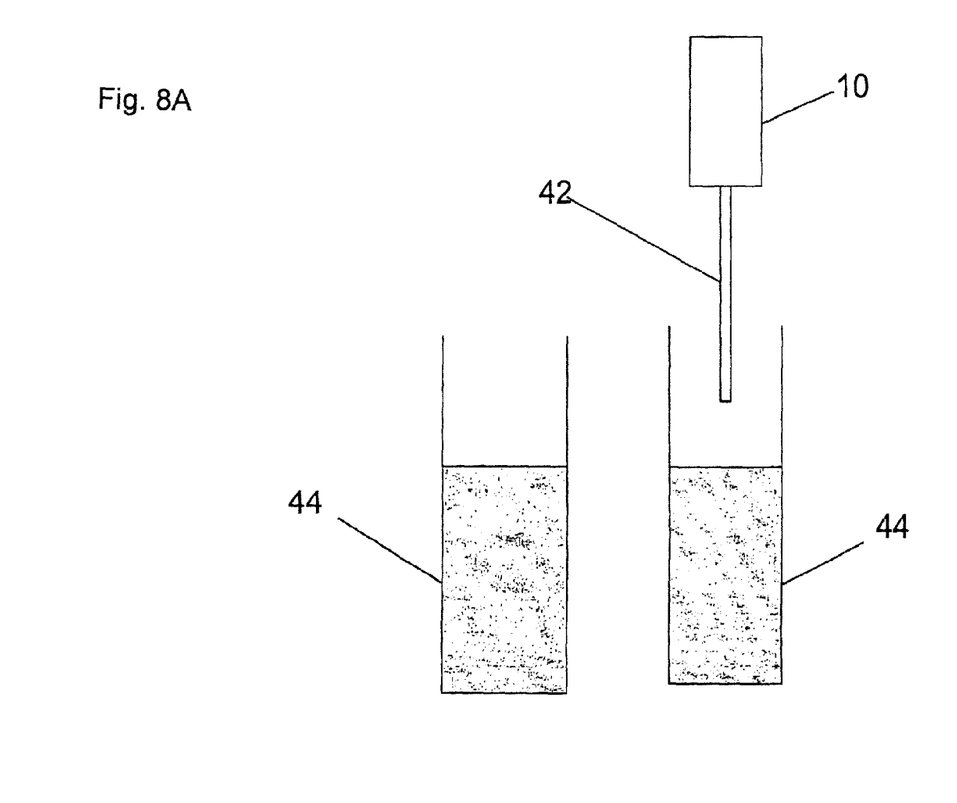
FIG. 8A illustrates one embodiment of the fluid distribution of the present invention.
Figure 8B:
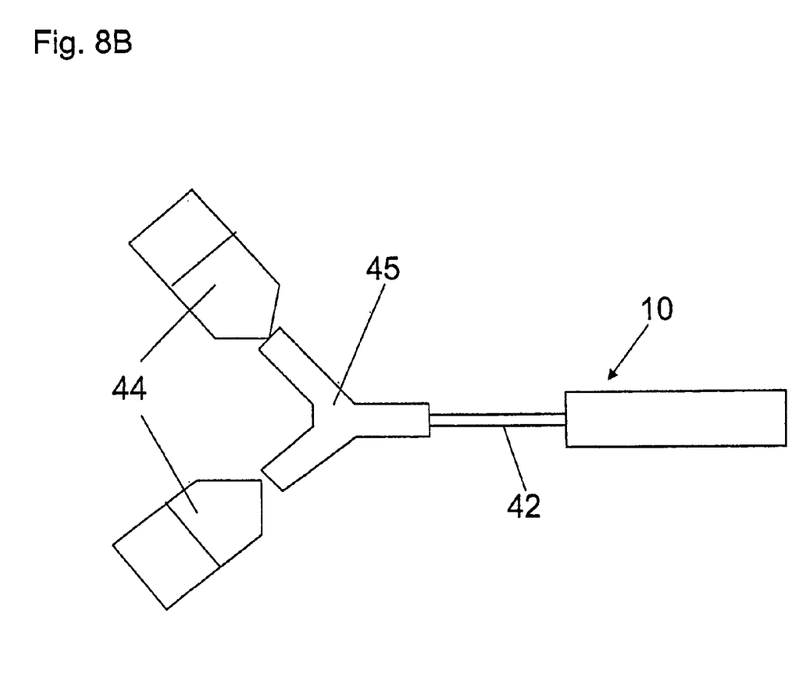
FIG. 8B illustrates another embodiment of the fluid distribution of the present invention.

Alternatively and as shown in FIG. 8A, the fluids can be each disposed in sealed vial(s) or cartridges 44. One cartridge can contain the collagen and/or gel and another cartridge, platelets or the platelet rich plasma. In one embodiment, the mixing and delivery device can be sequentially inserted into the vials and the desired quantity of fluid drawn into the device 10. In another embodiment, shown in FIG. 8B, the fluids are contained in the separate vials or cartridges 44 each in communication with a three-way portal 45. When the plunger of mixing and delivery device 10 is activated desired quantities of each fluid are simultaneously drawn from vials 44, through portal 45, injector 42 and into the mixing chamber of device 10. It should be appreciated that the fluids can be drawn into the tube by creating pressure on the opposite side of the mixer.

Figure 9:
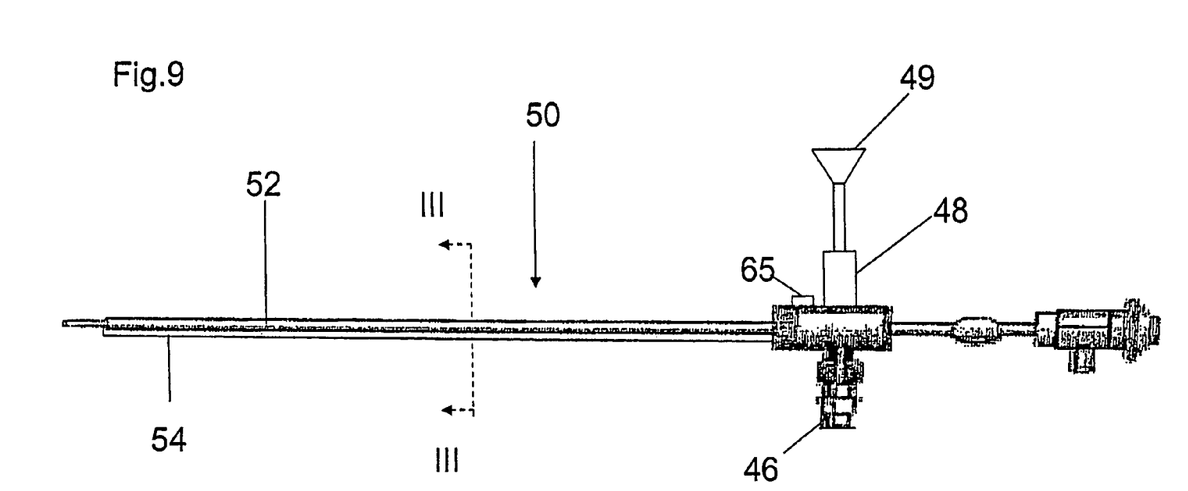
FIG. 9 is a perspective view of an embodiment of the delivery and mixing device for an arthroscopic sheath.
Figure 10:
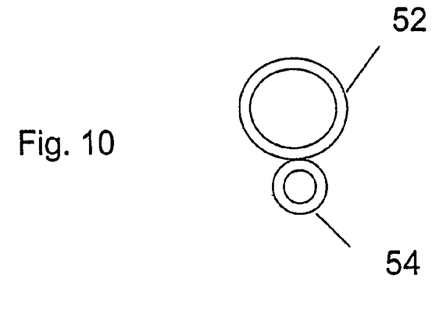
FIG. 10 is a cross-sectional view of the primary and secondary sheaths taken along line III-III of FIG. 9.

Referring to FIGS. 9 and 10, a preferred embodiment of a device 50 for mixing and delivering the viscous fluids for the arthroscopic repair of tissue is shown. A primary arthroscopic sheath 52 is used for the delivery of fluids, suction or a camera as is known. A first portal 46 communicates with sheath 52 to deliver fluids or supply air or suction. A secondary sheath 54 is disposed below primary sheath 52 and extends parallel to the axially length thereof. Secondary sheath 54 is used to deliver the collagen and platelet gel as described above. Secondary sheath 54 can be permanently or removably attached to the primary sheath. Although secondary sheath 54 is shown as being disposed below the primary sheath other positions are contemplated by the present invention.

Secondary sheath 54 has opposed ends, one end has a tip 56, which will be described further herein, and the other end 58 communicates with a second portal 48. The mixing and delivery device 10 loaded with the mixture is removably attachable to portal 48 to deliver the mixture to secondary sheath 54. Portal 48 includes an interlocking connection 49 to lock the mixing and delivery device 10 therein. As shown in FIG. 10, the diameter of the secondary sheath is smaller than the diameter of the primary sheath.

Figure 11A:
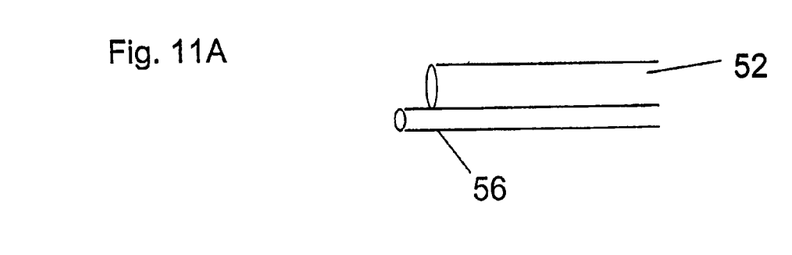
FIGS. 11A-11E are different embodiments of the tip of the secondary sheath of FIG. 9.
Figure 11B:
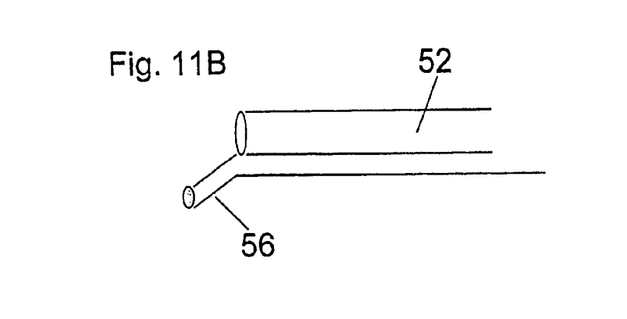
Figure 11C:
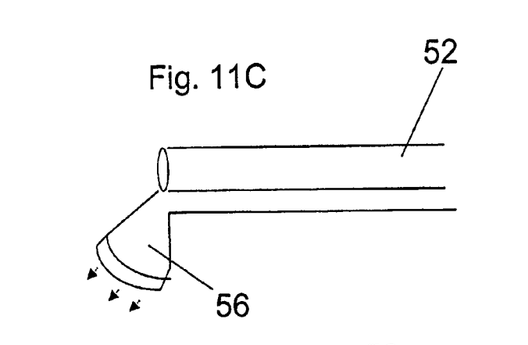
Figure 11D:
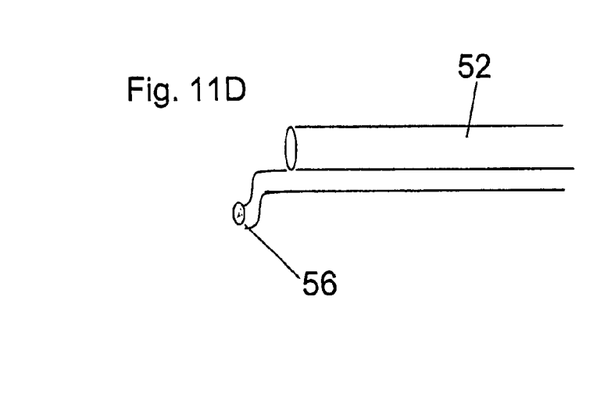
Figure 11E:
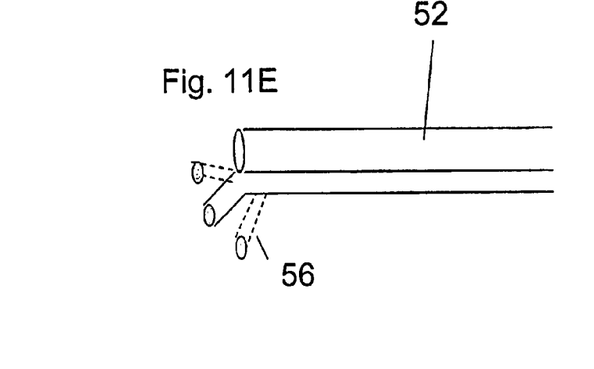

Referring to FIGS. 11A-11E, different embodiments of tip 56 are illustrated. As shown in FIG. 11A, tip 56 can be straight. Alternatively, as shown in FIG. 11B, tip 56 can be bent at an angle with respect to the primary sheath tip. The tip can be angled downward in a range of 0-90°, and more particularly, between 30 to 70°. The tip can be bent at 30° to match a standard lens angle or 70° to match a 70° lens of a camera sheath. The tip can also be fan-shaped as shown in FIG. 11C. Tip 56 can also be made of a flexible material so that it can be pushed and inserted into nooks or crannies of the joint as shown in FIG. 11D. In order for the surgeon to be able to change the direction of the tip to control the handpiece, tip 56 can be steerable as shown in FIG. 11E. When the sheaths are located at the injury site, the physician can direct the collagen mixture to the tear or rupture to deliver the same. Depending on the type of delivery desired the tip of the secondary sheath can have one of the above shapes.

Figure 12:
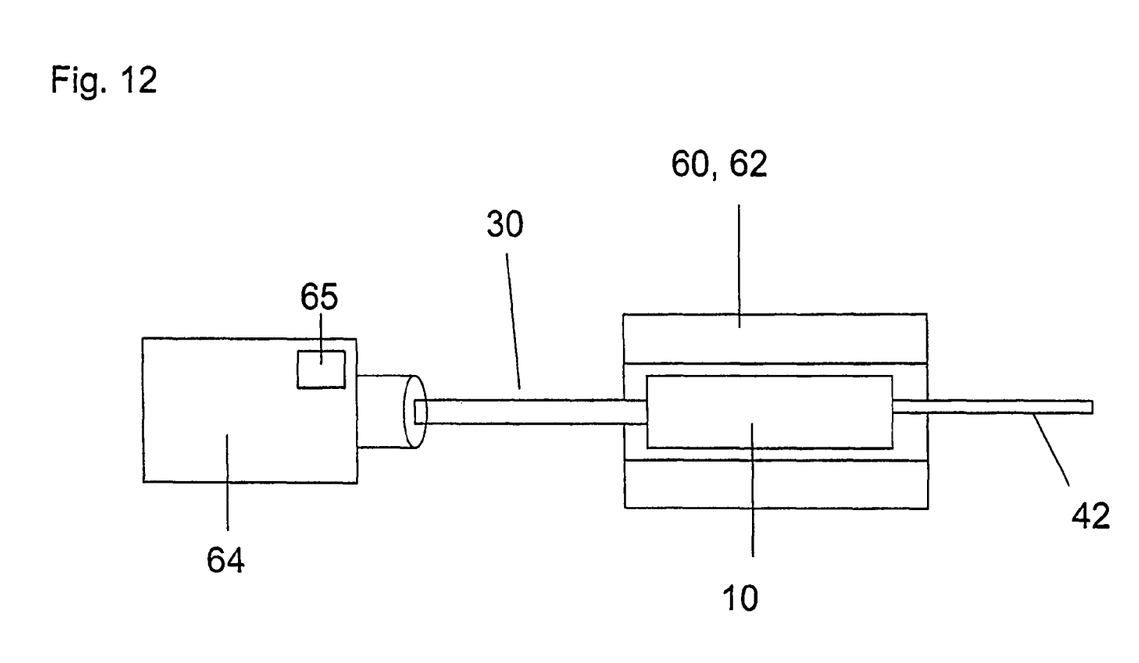
FIG. 12 is a top view of the mixing and delivery device disposed within a heating or cooling element.

As shown in FIG. 12, the syringe filled with the mixture can be placed in a heating bed 60 to heat the fluid. Drive shaft 30 of the plunger can be connected to a motor 64 which rotates the plunger and auger within the syringe. The heating element and motor can be located on a sterile table remote from the procedure site, but convenient to the operating physician. Mixing and heating the mixture gets the mixture to the desired viscosity, uniformity and temperature.

The viscosity of the injected fluid determines whether or not the mixture functions as an effective scaffold. If the viscosity is too low, the fluid will drip out of the target injury site, and will be of no use. If the viscosity is too high, the molecular structure of the fluid is ripped apart when injected through the injector or needle. The viscosity is determined by the initial collagen makeup and the degree of cross linking. The collagen makeup is done in the lab, and results in a solution roughly as viscous as corn syrup. The cross linking dictates the viscosity in that as the cross links are formed during the curing process, the molecules become more intertwined, and more resistant to flow. If too far advanced, these bonds are destroyed when injecting. A degree of cross linking must be attained in order to meet the minimum viscosity specification. Since, the rate of cross linking is temperature dependent, a time-heat method is used to control the viscosity.

The present invention contemplates different ways to heat the fluid, for example, an internal viscous heater, an external heater, or a thermal mass. The viscous heater operates by shear friction between the mixing element and the fluid. The external element is heated and surrounds all or a portion of the fluid container. The thermal mass is charged to an appropriate temperature, and then inserted to transfer heat. A viscous shear heater does not require additional components. The fluid is heated by running the mixer for a longer period of time. However, damaging the collagen-PRP matrix as it begins to crosslink may occur. Once the two chemical begin to crosslink, the rotation of the mixer could act to rip apart the bonds, so mixing should be carefully controlled.

A resistance heater generates heat when current passes though, i.e., by joule heating. Resistance heaters have well defined performance characteristics and can be controlled relatively easily. The electrical energy required is also well within the available energy stored in a 9V battery.

The thermal mass method can be implemented with an external mass, such as a block of aluminum, or with a fluid, such as the plasma. Here the energy is stored in the thermal mass, instead of the electric charge. This offers the advantage of being rechargable via a hot water bath, as well as, eliminating potentially complicated control aspects. It simplifies sterility aspects in the preparation stage as it is only a block of metal to autoclave. However it requires a sterile hot-water bath.

A resistive heating element has the ability to control heat output, as well as the existing presence of electrical storage for the motor. Heating element 60 can be a 5 W heater capable of heating the fluid to the necessary injection temperature in a short period of time, for example, 2-5 minutes. The system can be run open-loop, using either external measurement, or a specified time, based on initial temperature and experimental results. A production model could include closed loop electronics to control the temperature automatically. With closed loop control, a more aggressive heating pattern could be followed as well, potentially reducing the heating time as low as approximately 1 minute. A low-complexity design could be a hand-cranked mixer with a thermal mass heater. Although the heating element 60 is described as a resistive heating element, it should be appreciated that the device of the present invention contemplates a variety of heating designs in addition to those described above. Moreover, viscosity can be measured indirectly by drag on the motor. A viscosity sensor 65 (FIG. 12) could likewise be located within the motor, mixing tube, injection portal or other location.

After the desired temperature and viscosity has been reached the mixing and delivering device 10 is removed from the heating bed and located into portal 48 to deliver the heated and mixed fluid to the injury site via secondary sheath 54.

Alternatively, the mixing and heating device 10 can be inserted in a chilling element 62 in the same manner as above. The chilling element can keep the collagen and/or mixture cold until it is ready for use to avoid premature setting.

Chilling element 62 may have a refrigeration element designed to maintain the collagen component at a desired temperature, for example, 4° C. Conforming chill packs, a refrigeration element, gas, cold water circulation or other mechanical equivalents, are examples of cooling sources that can be incorporated in element 62. The cooling source surrounds a sterile core into which the collagen syringe can be kept until ready to mix with the platelets.

In order for the glue scaffold to adhere to the injured tissue it is necessary to remove fluid from the target site. Some strategies to meet this drying requirement are to wipe/sponge, remove moisture via suction, or blow dry the ligament. Wiping would use capillary action in a material to remove moisture from the operation site. A pressurized gas can provide a blow drying technique to force fluid particles off of the operation site with a stream of air. It also facilitates evaporation through the introduction of a gas with a low moisture partial pressure. However, the operating arena may not have a source for pressurized gas. In that case and to make the device portable, the use of a compressed gas cartridge may be necessary. Typical gas cartridges are filled at 300 psi. therefore, it may be necessary to incorporate a flow regulator in order to control flow rate and prevent damage to the patient tissue. Alternatively the site can be dried by using a suction source. In the embodiment of FIG. 9, a pressurized gas delivered through primary sheath 52 or a suction source applied to primary sheath 52 can be used to dry the target site prior to delivering the scaffold.

Figure 13:
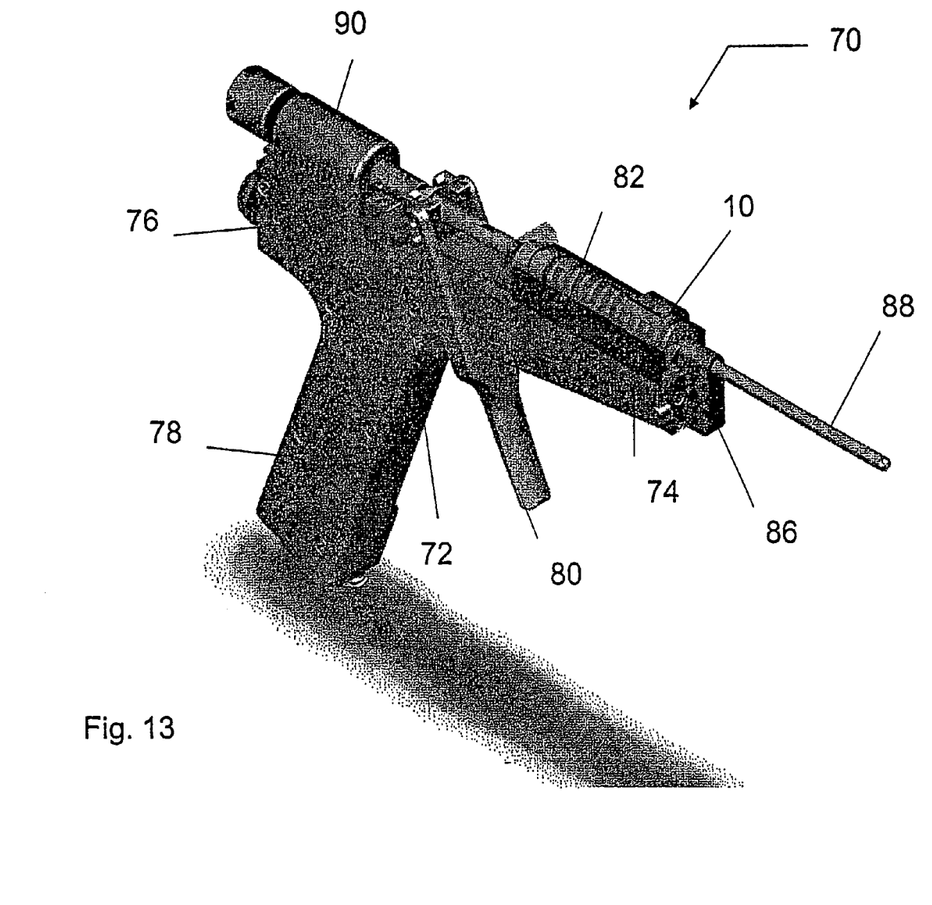
FIG. 13 is a perspective view of yet another embodiment of a mixing and delivery device of the present invention.
Figure 14:
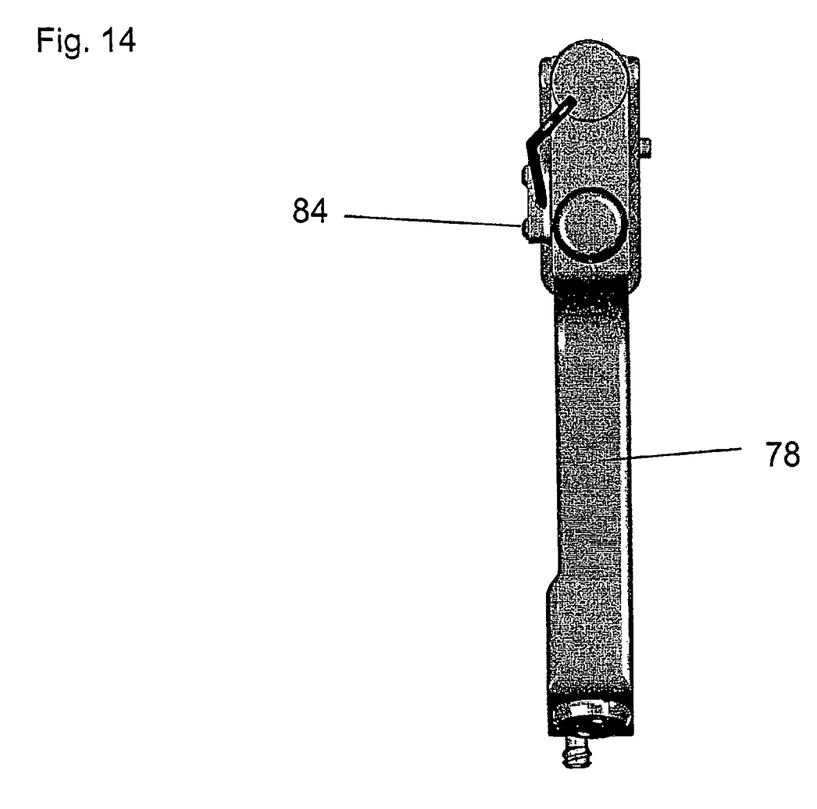
FIG. 14 is a back view of the device of FIG. 13.
Figure 15:
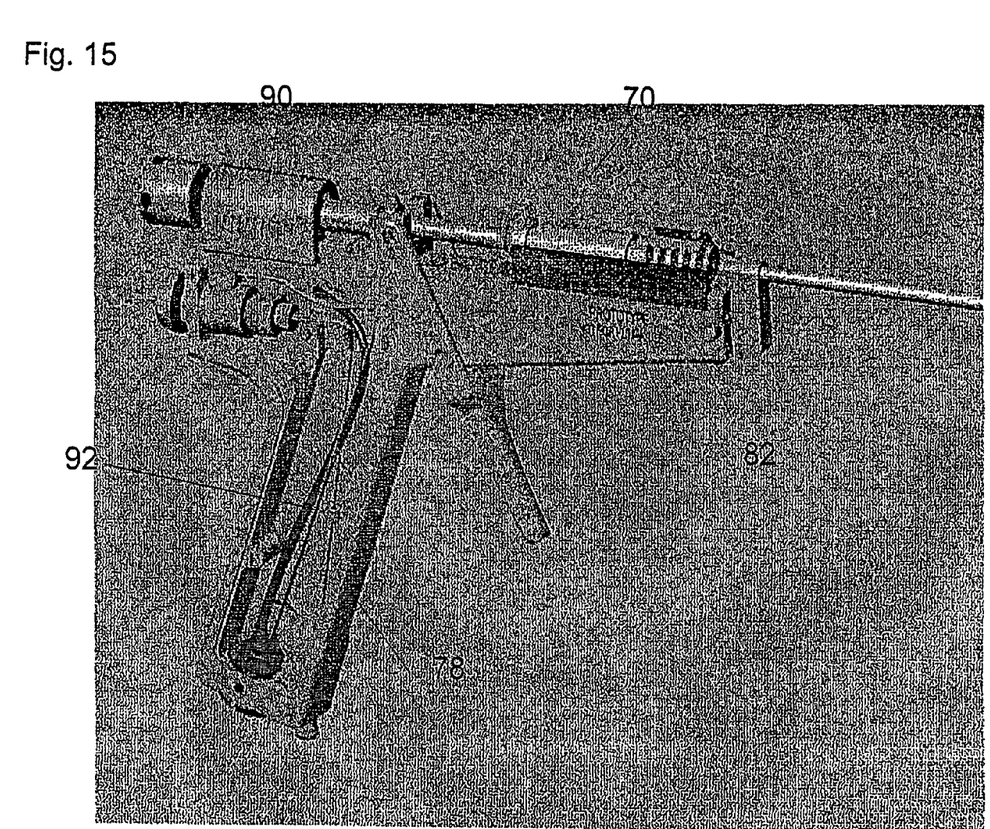
FIG. 15 is a perspective view of the device of FIG. 13 with the cover of the handle removed.

Referring to FIGS. 13-15 another embodiment of the present invention is shown. A hand-held device 70 for mixing and delivering the viscous fluids includes a barrel 72 having ends 74 and 76. The mixing and delivery device 10 is removably located at end 74 of the barrel. A handle 78 is formed at the other end of the barrel. A trigger mechanism 80 is pivotally connected to the barrel 72. Trigger 80 communicates with a shoulder 31 (FIG. 5) of shaft 30 such that when the user activates trigger 80 it pushes plunger 16 into tube 12 to compress auger 14 and dispense the fluid through injector 42.

A heater 82 is mounted on barrel 72 and communicates with mixing and delivering device 10. As previously described herein, heater 82 heats the fluids to control the viscosity of the same. A battery 84 located on or within barrel 72 can provide the power source for heater 82.

A mechanism 86 for drying the injury site is also removably located on the barrel. Dryer 86 can be a nozzle that snaps on barrel end 74. Nozzle 86 includes a sheath 88 that receives the needle or injector 42 when the nozzle is fitted on the device. A $CO_2$ cartridge and flow regulator can be located within handle 78 and can connect with sheath 88 via tubing. Alternatively, handle 78 can include a port for connecting a source of gas or suction to dry the injury site.

As discussed above, it may be necessary to incorporate a flow regulator in order to control flow rate and prevent damage to the patient tissue. A $CO_2$ nozzle was designed to both protect the fluid carrying needle and to deliver the $CO_2$ to the target site. The nozzle uses thin-wall steel tubing as an outer case. The nozzle connects to the body of the gun using an out-of line quick-connect fitting that also serves to stabilize the nozzle. The $CO_2$ enters the nozzle from the bottom, and proceeds to the tip, where a dome-shaped fitting centers the needle while allowing $CO_2$ to pass. The needle pierces a septum on the back of the nozzle, which prevents the $CO_2$ from flowing out the wrong end.

A motor 90 to mix the fluids is located on the barrel as previously described. Motor 90 can be driven by battery 84 or connectable to a remote AC power source via wiring 92.

Figure 16A:
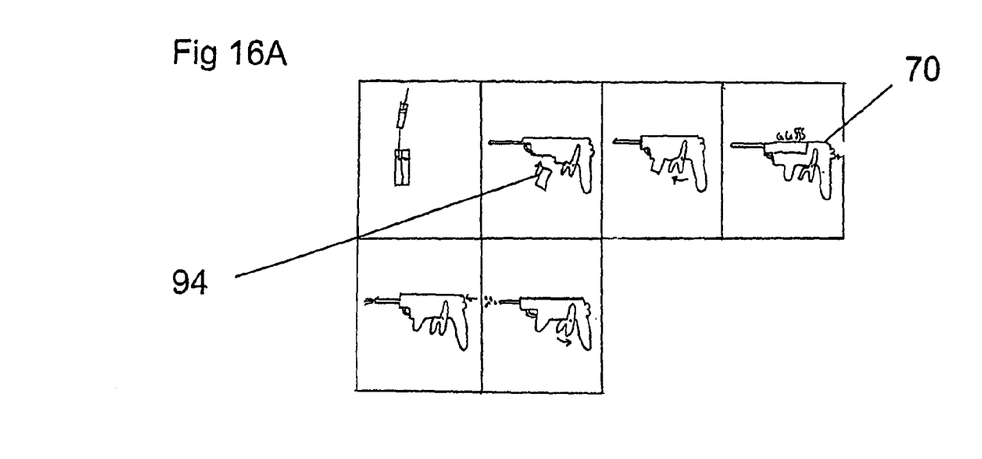
FIGS. 16A and 16B illustrate an alternative embodiment of a mixing and delivery device according to the present invention.
Figure 16B:
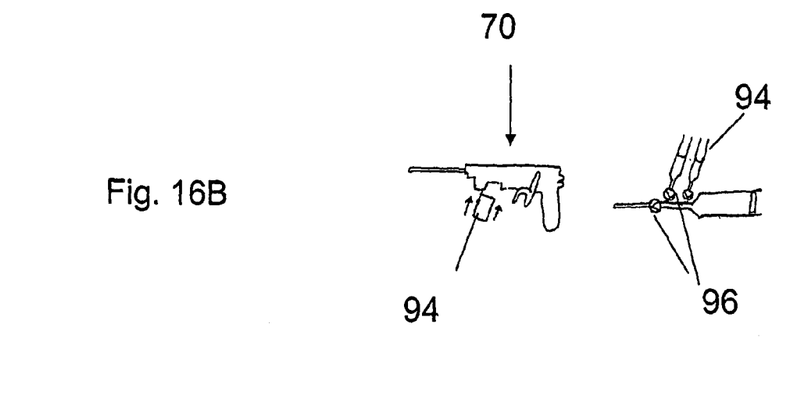

Referring to FIGS. 16A and 16B, an alternative way to deliver the collagen and PRP is shown. A plurality of preloaded cartridges 94 each having a desired quantity of collagen and PRP can be provided. A one-way valve 96 communicates with a respective cartridge and the mixing and delivery device 10. When the valves are open the plunger can be used to act as a displacement pump to draw the fluids simultaneously or in parallel into the mixing device. Another valve disposed downstream of the cartridges can remain closed until it is time to dispense the mixture.

In order for the device to be used in an operating room environment, it must be sterile. Therefore, the device of the present invention, i.e., the gun, mixing and delivery device can be made of disposable and/or autoclavable parts. The gun shell and the needle would have to be sterilized, as they would be in direct contact with bodily fluids. Also, the battery, and $CO_2$ canister would have to be replaced once the stored element was exhausted. The more expensive parts, such as the needle, tip, motors, etc, can be sterilized. The cheaper plastic, injection molded parts such as the auger/injector system, could be disposable. In addition, the layout of the operating room makes any secondary, external operation more difficult. The various parts can be sterilized and packaged in a kit that can be sealed and brought to the operating arena.

In use, one process of mixing the collagen and platelet rich plasma (PRP) and injecting it once it has reached the appropriate viscosity is as follows. First, dip the needle into the collagen and extract an appropriate amount thereof, for example, approximately 1.5 ccs. Then, dip the needle into the PRP and extract a desired amount, for example, 1.5 ccs of plasma. Point the gun upwards and purge the syringe of any air. Then snap on a $CO_2$ nozzle, mix the scaffold, for example, for 10 seconds, and heat the scaffold (i.e., for 4 minutes. The system is then purged of any unmixed fluid that has remained in the needle. The ligament is dried via, for example, the $CO_2$ flow, and the mixtures of collagen and PRP is injected at the target site.

The present invention also contemplates a visual feedback means that will enable the doctor to verify that the mixture must be injected within a certain time frame either through for example, lights or a display. Additionally, the device could have means to control the viscosity using feedback from measuring the power draw on the motor. A pressure regulator can be included in addition to the flow regulator within the $CO_2$ delivery system to better control the pressure of the fluid released over time. Additionally, a precise specification of the flow rate and pattern required should be determined by the doctor to ensure that the canisters will provide enough fluid for the entire procedure time.

The integration of all the components into a cohesive form allowed for convenient use by the operating doctor. The main considerations are intuitive control location, ergonomics, and routing of the high-pressure $CO_2$. In order to allow for comfortable, but precise manipulation by the doctor, a pistol-grip form was selected. The intuitive control allows doctors to use the gun as any other device. The controls are located in an ambidextrous fashion, with the exception of the heater switch. The heater switch is located on the side. The $CO_2$ lines are routed so as to be as short and straight as possible. This is to minimize the possibility of leakage or damage to the tubing, which can lead to the catastrophic failure of the $CO_2$ system.

The integration methods described earlier, the single embedded syringe-mixer and the dual-cartridge displacement-pump/mixer, should be considered in terms of the overall process and considerations to sterility. With regard to dimensions associated with device, the most critical dimensions are associated with the sealing in the syringe and in the drive train/gear system. The inner dimension for the rotary seal on the plunger should ideally be made to within 0.001 in. so that the friction associated with the seal remains as uniform as possible. Critical dimensions associated with the drive train are the gear spacing and the allowable shaft misalignment. The spacing between the pinion and spur gear (not shown) should be held to within 0.005 in. to insure the proper spacing. Binding will occur if the shaft has worse than 0.008 radians axial misalignment with the bearing. Since the end of the shaft is constrained by the syringe, it must be put on the gun with no more than 0.04 in. offset from the shaft.

The majority of the components of the device can be manufactured using rapid prototyping techniques, for example, injection molded. The left and right shell, the $CO_2$ canister cover, the left and right syringe pusher blocks, the trigger, and the front of the device can be made using stereo lithography. The collapsible auger can be made, for example, using selective laser sintering because it is subjected to higher stresses. The mixing and delivery device can be made of Radel®, Peek®, or Tecapro®, or another high performance medical grade plastic. The bearing and the seal piston can be machined from Delrin.

The present invention provides a unique injection system for the enhanced ACL repair. Although the device and system of the present invention has been described for repairing an injured ACL, it should be appreciated that it can be used for numerous different procedures, for example, fibrin sealants in cardiac surgery. The system of the present invention integrates a sample extractor, mixer, dryer, heater, and injector into one unit. Shown by experimental data, the injection system is capable of performing the enhanced repair processes while remaining totally sterile. By coupling features like a viscosity sensor and a thermometer, the system can be used to monitor the process and give surgeons feedback if required. Also, the system is specialized for mixing of highly viscous solutions, which makes it a powerful tool for various processes like bone cement or epoxy mixing.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A device to be disposed on an arthroscopic sheath for mixing and delivering viscous fluids for the arthroscopic repair of tissue, the device comprising:
   a secondary elongated sheath removably disposed along an axial length of the arthroscopic sheath, the secondary sheath having opposed ends, one of the ends of the secondary sheath having a tip, said tip being located at an operating end of the arthroscopic sheath,
   a mixing tube for containing the fluids to be mixed, the tube including a mixing chamber and being in fluid communication with the secondary sheath, and
   a mixing element movably disposed within the mixing chamber for mixing the fluids, wherein the mixing element is a collapsible auger or a compressible auger.

2. The device of claim 1, further comprising a plunger movably disposed within the tube for delivering a mixture of the fluids to the tip of the secondary sheath.

3. The device of claim 1, wherein the mixing tube defines an internal bore along its length.

4. The device of claim 1, wherein the mixing element is a collapsible auger.

5. The device of claim 1, wherein the mixing tube has a proximal and a distal end.

6. The device of claim 5, wherein the mixing element is a compressible auger movably disposed within the tube, one end of the auger being free at the distal end of the tube, and a plunger movable within the tube, a first end of the plunger being in communication with the other end of the auger and a second end of the plunger extending from the proximal end of the tube, wherein when the plunger is moved axially within the tube the auger also moves axially and the auger is compressed.

7. The device of claim 1, wherein the mixing element is rotatably and axially movable within the mixing chamber of the tube.

8. The device of claim 1, wherein the fluids to be mixed are collagen and platelet rich plasma.

9. The device of claim 1, wherein the tube includes a quantity of collagen gel.

10. The device of claim 1, wherein the tube comprises a syringe having an injector for delivering the mixed fluids from the mixing chamber to the secondary sheath.

11. The device of claim 10, further comprising a portal disposed at the other end of the secondary sheath, the syringe being removably positioned within the portal.

12. The device of claim 11, further comprising an interlocking connection between the portal and injector of the syringe.

13. The device of claim 1, wherein the secondary sheath is disposed below and extends parallel to the length of the arthroscopic sheath.

14. The device of claim 1, wherein the tip of the secondary sheath is straight.

15. The device of claim 1, wherein the tip of the secondary sheath is bent.

16. The device of claim 1, wherein the end of the tip is bent at an angle within the range of 0 to 70 degrees.

17. The device of claim 1, wherein the tip of the secondary sheath is fan-shaped.

18. The device of claim 1, wherein the tip of the secondary sheath is flexible.

19. The device of claim 1, wherein a diameter of the secondary sheath is less than the inner diameter of the arthroscopic sheath.

20. The device of claim 1, further comprising a heating element for heating the fluids in the tube.

21. The device of claim 1, further comprising a cooling element for chilling the fluids in the tube.

22. The device of claim 1, further comprising drive means removably attached to the mixing element for rotating the same within the tube.

23. The device of claim 1, wherein the secondary sheath is disposed below and extends parallel to the length of the arthroscopic sheath.

* * * * *